United States Patent [19]

Kötzsch et al.

[11] 4,060,536
[45] Nov. 29, 1977

[54] METHOD OF PREPARING N,N'-BIS-TRIMETHYLSILYLUREA

[75] Inventors: Hans-Joachim Kötzsch, Rheinfelden; Hans-Joachim Vahlensieck, Wehr, both of Germany

[73] Assignee: Dynamit Nobel Aktiengesellschaft, Troisdorf, Germany

[21] Appl. No.: 746,023

[22] Filed: Nov. 30, 1976

[30] Foreign Application Priority Data

Dec. 1, 1975 Germany .............................. 2553932

[51] Int. Cl.$^2$ .............................................. C07F 7/10
[52] U.S. Cl. .............................................. 260/448.2 E
[58] Field of Search .................................. 260/448.2 E

[56] References Cited

U.S. PATENT DOCUMENTS 3,992,428  11/1976  Müller et al. ................. 260/448.2 E Primary Examiner—Paul F. Shaver
Attorney, Agent, or Firm—Burgess, Dinklage & Sprung

[57] ABSTRACT

An improvement in a process for preparing N,N'-bis-trimethylsilylurea by reaction of urea with hexamethyldisilazane at an elevated temperature accompanied with ammonia evolution wherein the reaction is carried out in the presence of an acid catalyst.

10 Claims, No Drawings

METHOD OF PREPARING N,N'-BIS-TRIMETHYLSILYLUREA

BACKGROUND OF THE INVENTION

Field of the Invention

This invention relates to a method of preparing N,N'-bis-trimethylsilylurea by reaction of hexamethyldisilazane at an elevated temperature accompanied with ammonia evolution. More particularly, this invention relates to such a process carried out in the presence of an acid catalyst, e.g., a Lewis acid, hydrogen ion yielding acid, or ammonium salt thereof. This invention is particularly concerned with the realization of high yields of relatively pure N,N'-bis-trimethylsilylurea in a relatively short period of time without entailing substantial cost.

DISCUSSION OF THE PRIOR ART

The N,N'-bis-trimethylsilylurea that can be made by the method of the invention is of importance in polymer chemistry, especially as a protective-group reagent in the preparation of semisynthetic penicillins and cephalosporins.

The preparation of N,N'-bis-trimethylsilylurea in laboratory amounts by the reaction of urea with neutral hexamethyldisilazane is known (Zeitung anorg. allg. Chemie 321 (1963) pages 208 to 216). It has been found, however, that a product prepared in accordance with this publication, for which a "crude yield" of 98% is reported after a 38-hour reaction, but no pure yield, does not satisfy the requirements which should be met by a protective-group reagent for penicillin chemistry. A product that would in any way be usable could then be obtained only if the crude product obtained by the procedure described in the above-cited literature were subjected to a vacuum sublimation procedure at elevated temperature; even then, however, the product thus purified still decomposes at a temperature that is about 9° C below the 232° C melting temperature of pure N,N'-bis-trimethylsilylurea.

In this procedure, the high volatility of the substance, which results in appreciable sublimation losses, is a handicap. Furthermore, losses of the substance occur due to the considerable rate of decomposition of N,N'-bis-trimethylsilylurea to trimethylsilylisocyanate and hexamethyldisilazane, for example. Additional disadvantages are the unavoidable technical cost of this kind of refinement by sublimation, and the considerable sublimation heat which requires a correspondingly high input of heating and cooling energy. In spite of this great difficulty, an end product of unsatisfactory quality is obtained, which manifests itself in the presence of unreacted starting products, especially urea, and in an excessively low silylation activity (between 60 and 84%).

The above-described disadvantages occur even when absolutely pure starting materials are used. The course of the reaction proves additionally to be greatly dependent, in the known process, on the composition of the starting materials. In particular, the urea must contain no moisture. Depending on the crystal activity of the urea used and on the purity of the hexamethyldisilazane, startup times for the reaction have been observed to be from 8 to 26 hours, and the reaction times to be between 11 and 36 hours. Such long reaction times are not suitable for the technical performance of the process. The good reaction results described in the above-cited literature could only be achieved with thoroughly dried, finely ground urea and absolute hexamethyldisilazane. With starting substances of various technical qualities, appreciably different reaction conditions have been observed, and far poorer product qualities have been obtained.

SUMMARY OF THE INVENTION

Broadly, this invention contemplates an improvement in a process for the preparation of N,N'-bis-trimethylsilylurea by reaction of hexamethyldisilazane with urea at an elevated temperature accompanied with ammonia evolution, which improvement comprises carrying out the process in the presence of an acid catalyst.

By the application of the method of the invention, decided improvements are obtained in the product qualities and a rapid and regular course of reaction, even when the starting products are of technical purity.

The premature cessation of the reaction, such as is always observed when catalysts of the invention are not used, no longer takes place. Instead, the batch undergoes a complete reaction under the conditions of the invention, in a relatively short time, until all of the urea has reacted.

The product is thus obtained in yields of 96 to 100%. It has a melting point of 231° to 232° C, and without any further purification it can be used immediately, without limitation, as a protective-group reagent in penicillin chemistry. The silylation activity of the N,N'-bis-trimethylsilylurea prepared by the method of the invention, which is essential to its use for this purpose, is 97 to 100%.

The catalysts of the invention furthermore surprisingly offer the advantage of selective activity as an accelerator of the reaction of the formation of N,N'-bis-trimethylsilylurea, while competing reactions, such as the formation of trimethylsilylisocyanate, for example, are not promoted. This effect of the method of the invention is another reason for which the N,N'-bis-trimethylsilylurea is obtained in a higher yield and purity than in the process known hitherto.

Catalysts in the meaning of the present invention are Lewis acids of the halogens with the elements of the third to fifth group of the Periodic System, and the hydrogen ion yielding acids, in some cases in the form of their ammonium salts. Especially preferred are the hydrogen halides, sulfuric acid, phosphoric acid, acetic acid, and the simple as well as complex halides of the elements boron, aluminum, silicon, titanium, zirconium and phosphorus, as well as their addition compounds, such as etherates, for example.

Examples of protic, i.e., hydrogen ion forming acids, from among the substances of inorganic chemistry are the hydrogen halides, such as hydrochloric acid, hydrobromic acid and hydroiodic acid, the oxygen acids of the halogens, such as chloric acid, perchloric acid, bromic acid and iodic acid, the acids of sulfur, such as sulfurous acids and sulfuric acid, the phosphoric acids, such as orthophosphoric acid, and all ammonium salts of the above acids. Catalytically active Lewis acids are, for example, boron halides, especially boron trifluoride, boron trichloride, boron trifluoride etherate, etc.; also, aluminum compounds, especially aluminum chloride, ethoxyethyl aluminum chloride, etc.; silicon compounds, especially halogen silanes, such as, for example, tetrachlorosilane, methyltrichlorosilane, dimethyldichlorosilane, trimethylchlorosilane etc. Also titanium and zirconium halides, especially titanium tetrachloride, titanium trichloride, zirconium tetrachloride and phosphorus halogen compounds, especially $PCl_3$, $POCl_3$ and $PCl_5$, are suitable as catalysts.

It is to be understood with respect to the generic, subgeneric or specific acids disclosed herein that each and every member of the group functions as a catalyst independent of the other members of the group. For example, while hydrogen halides are described generically, it is also meant that each hydrogen halide can be employed independent of the other. Thus, HCl, HBr and HI are collectively and separately contemplated with reference to one another and the genus. Thus it is as correct to say that hydrogen chloride, hydrogen bromide and hydrogen iodide form a group of suitable catalysts as it is to say that hydrogen chloride and hydrogen bromide or hydrogen iodide form a group. No inferences are to be made from the grouping of the various members, as an infinite number of groups are intended by this disclosure.

From among the substances of organic chemistry, aliphatic mono- and dicarboxylic acids and their ammonium salts are especially active catalytically in the sense of the method of the invention, e.g., formic acid, acetic acid, oxalic acid, succinic acid; however, benzoic acid can also be used.

Generally speaking, the aliphatic mono- and dicarboxylic acids will have between 1 and 18 carbon atoms in the chain. Where an aromatic acid is employed, the aromatic acid will have between 6 and 18 carbon atoms in the ring. Especially contemplated are aromatic mono- and dicarboxylic acids of a $C_6$ aromatic ring.

The amount of the catalyst can vary between 20 ppb (parts per billion) and 2 grams per liter of substrate; amounts between 200 ppb and 200 ppm per liter of substrate are used preferentially.

The process of the invention is performed with the exclusion of moisture simply by mixing urea with a slight excess of hexamethyldisilazane to which the catalyst is added prior to use. It matters not which of the two reactants is added to the other. Neither is the purity of the starting products of any importance and technical qualities can be used, especially, the hexamethyldisilazane does not have to be subjected to any special purifiction beforehand. The reaction mixture is then raised to the boiling temperature, with stirring, and refluxed, the boiling point of the hexamethyldisilazane establishing itself. During the reaction, pure ammonia escapes in a steady stream and is sold for reuse. During the reaction, the urea passes completely into solution, and N,N'-bis-trimethylsilylurea is produced in great volume in the form of fine needles. The isolation of the product can be undertaken by simple distillation, filtration or centrifugation of the fluid components by conventional methods for their removal. A preferred method of separation consists in distilling out the fluid components with stirring by means of known stirrers for solids.

Stirrer vessels equipped with reflux condensers and systems for carrying off ammonia are used as apparatus for the performance of the reaction, which, if desired, can also be equipped with stills for the final removal of excess hexamethyldisilazane. The stirrers used can be not only impeller types, but also, and especially, wall-riding anchor stirrers, single-stage or multi-stage paddle stirrers, or horizontal paddle shafts, as in paddle driers for example.

When the catalysts of the invention are used, the reaction starts up without any great delay, and completes itself in 4 to 8 hours, yielding very pure qualities. The product thus obtained complies, without any further refining operations, with the quality requirements for use in penicillin chemistry.

Generally speaking, the reaction is carried out at a temperature between 20° C and 140° C, preferably between 50° C and 130° C, for as short a period of time as 30 minutes to up to about 40 hours. The process can be carried out at subatmospheric pressure, atmospheric pressure, or superatmospheric pressure. Generally speaking, atmospheric pressure is desired. When the process is carried out at subatmospheric pressure, a pressure of between 30 and 760 Torr, preferably between 80 and 760 Torr, is generally employed. The process is generally carried out using a stoichiometric amount of urea and hexamethyldisilazane although it is preferred to use the hexamethyldisilazane in excess. Generally speaking, a 0 to 12 molar excess of hexamethyldisilazane is suitable.

The process can be conducted without the use of a solvent or it can be conducted in the presence of a solvent of the reaction medium. Where a solvent is to be employed, the solvent can be any one of the following types of solvents:

EXAMPLES

In order to more fully illustrate the nature of the invention and the manner of practicing the same, the following examples are presented:

EXAMPLE 1

A jacketed flask of 6 liters capacity, heated by a thermostat, equipped with a bottom drain, an internal thermometer, a two-stage paddle stirrer with slanting paddles, and a reflux condenser with a gas removal tube leading to a receiver operating with dilute sulfuric acid for the absorption of ammonia, is charged at about 20° C with 600 g of urea (technical, 3 mm diam., 0.3% moisture) and 3200 g of 100% hexamethyldisilazane in which 20 ppm of trimethylchlorosilane has been dissolved. Then the stirrer is started up at 130 rpm and the temperature is increased. The mixture begins to react as soon as its temperature rises above 62° C, which is manifested by an increasing production of ammonia. Finally a boiling temperature of 116°–117° C establishes itself, at which the reaction goes to completion within 4 hours, during which the developing N,N'-bis-trimethylsilylurea settles out in the form of an easily stirred, voluminous white precipitate. At the end of the reaction the internal temperature rises to 126° C and ammonia stops forming. Titration of the sulfuric acid receiver shows the theoretically calculated amount of ammonia.

At this moment the reflux condenser is replaced with a distillation bridge, the stirrer is set at 30 rpm, and the excess hexamethyldisilazane is distilled out (at the end in a vacuum of up to about 200 Torr for a short period). In all, 1569 g of distillate is obtained, with a boiling point of 126° C.

The needle-like crystalline N,N'-bis-trimethylsilylurea remaining in the flask is cooled down to 20° to 30° C and removed through the bottom drain valve. The yield amounts to 2012 g (98.6%) of shiny, white needles of a melting point of 231°–232° C.

TESTING

1. The shaking of 10 g with 20 ml of trans-dichloroethylene and gas chromatography of the filtrate showed less than 0.1% of trimethylsilylisocyanate, less than 0.02% of hexamethyldisilazane, and less than 0.01% of hexamethyldisiloxane in the product.

2. The silylation activity (measured on phenol by transformation to trimethylphenoxysilane by dissolving 100 mg of N,N'-bis-trimethylsilylurea in 20 ml of an anhydrous solution of 0.5% of benzoic acid ethyl ester and 3% of phenol in acetic acid ethyl ester, one hour of agitation of the mixture, and then evaluation by gas chromatography), proves to be, for the product prepared in accordance with the invention in Example 1, 99% (plus or minus 1%).

The product is thus suitable for use as a reagent in penicillin chemistry.

EXAMPLE 2 (for purposes of comparison)

600 g of freshly pulverized urea and 3200 g of completely neutral 100% hexamethyldisilazane were treated as described in Example 1.

When the mixture was heated, no reaction took place until after it had been refluxed for more than 7 hours at approximately 126° C. The internal temperature then diminished to 125° C, and not until after 22 hours of reaction did it rise again to 126° C, when the mixture yielded no more ammonia. At the time approximately 91% of the theoretically calculated amount of ammonia had been produced (determined by titration of the sulfuric acid receiver). Then the excess hexamethyldisilazane was distilled out. In all, 1682 g of distillate melting at 126° C was obtained. The N,N'-bis-trimethylsilylurea was produced in a quantity of 1871 g (92%) in the form of shiny white needles whose melting point (with decomposition) was 222° C.

TESTING

1. The shaking of 10 g with 20 ml of trans-dichloroethylene and gas chromatography of the filtrate showed about 0.7% of trimethylsilylisocyanate, less than 0.02% of hexamethyldisilazane, and less than 0.01% of hexamethyldisiloxane in the product.

2. The silylation activity (measured on phenol by transformation to trimethylphenoxysilane by the dissolving of 100 mg of N,N'-bis-trimethylsilylurea in 20 ml of an anhydrous solution of 0.5% of benzoic acid ethyl ester, 1 hour of abitating the mixture, and then evaluation by gas chromatography) was found to be 82% (plus or minus 1%) in the product prepared in Comparative Example 2 by the method of the state of the art.

This quality is unsuitable for use in penicillin chemistry. EXAMPLE 3

The procedure of Example 1 is repeated with 96% hexamethyldisilazane (remaining 4% hexamethyldisiloxane) containing 40 ppm of ammonium chloride in colloidally dissolved form.

The reaction starts as soon as the temperature rises above 79° C. A boiling temperature of 118° C establishes itself, at which the reaction is completed within 6 hours. The end of the reaction is recognizable by the increase of the internal temperature to about 125° C. Titration of the sulfuric acid receiver shows the theoretically calculated amount of ammonia has been formed.

Then 1582 g of excess hexamethyldisilazane is distilled out (91% pure, remainder about 9% of hexamethyldisiloxane). N,N'-bis-trimethylsilylurea precipitates in a yield of 2019 g (99%) with a melting point of 231° C.

The product contains less than 0.1% of trimethylsilylisocyanate, less than 0.03% of hexamethyldisilazane and less than 0.01% of hexamethyldisiloxane. Its silylation activity amounts to 98.4% (plus or minus 1%).

EXAMPLE 4

The procedure of Example 1 is followed using 90% pure hexamethyldisilazane (remainder approx. 10% of hexamethyldisiloxane) to which 60 ppm of acetic acid (100% pure) has been added.

The reaction starts up as soon as the temperature rises past 77° C. A boiling temperature of 114° C establishes itself, at which the reaction is completed within 6 hours. The end of the reaction is recognizable by the increase of the internal temperature to about 120° C. Titration of the sulfuric acid receiver shows the theoretically calculated amount of ammonia to have formed.

Then 1580 g of excess hexamethyldisilazane (73% pure, remainder approximately 27% of hexamethyldisiloxane) is distilled out. N,N'-bis-trimethylsilylurea precipitates in a yield of 2008 g (98.3%) with a melting point of 230°-231° C.

The product contains less than 0.1% of trimethylsilylisocyanate, less than 0.02% of hexamethyldisilazane and less than 0.02% of hexamethyldisiloxane. Its silylation activity amounts to 97.6% (plus or minus 1%).

EXAMPLE 5 (comparative example)

The procedure of Example 1 was followed with 3200 g of completely neutral, 90% hexamethyldisilazane (remainder approximately 10% of hexamethyldisiloxane).

Upon heating no reaction took place until the mixture had been refluxed for more than 24 hours at 123° C, whereupon the internal temperature diminished to about 120° C, rising slightly to about 122° C after 36 hours of reaction, when no more ammonia was given off. Titration of the sulfuric acid receiver showed that approximately 81% of the theoretically calculated amount of ammonia had been liberated.

Then 1876 g of excess hexamethyldisilazene (84% pure, remainder about 16% of hexamethyldisiloxane) was distilled out. The N,N'-bis-trimethylsilylurea was obtained in a yield of 1660 g (82%) with a boiling point of 212° C (with decomposition).

The product contains about 0.8% of trimethylsilylisocyanate, less than 0.02% of hexamethyldisilazane and less than 0.02% of hexamethyldisiloxane. Its silylation activity amounts to 63% (plus or minus 1%).

EXAMPLES 6 to 13

The procedure of Example 1 was followed using 96% pure hexamethyldisilazane containing 60 ppm of boron trichloride, titanium tetrachloride, silicon tetrachloride, aluminum chloride, phosphorus oxychloride, sulfuric acid, orthophosphoric acid and hydrogen bromide, respectively. Table 1 below shows the experimental results obtained therewith.

Table 1

Yields and silylation activities of N,N'-bis-trimethylsilylurea prepared by the method of the invention with various catalysts, showing start-up and reaction times.

| Example No. | Catalyst | Start-up time (h) | Reaction time (h) | Yield % | Silylation activity % |
|---|---|---|---|---|---|
| 6 | HCl$_3$ | 0.4 | 7 | 97.2 | 96 |
| 7 | TiCl$_4$ | 0 | 5 | 99.1 | 100 |
| 8 | SiCl$_4$ | 0 | 6 | 99.0 | 100 |
| 9 | AlCl$_3$ | 1.2 | 8 | 97.0 | 96 |
| 10 | POCl$_3$ | 1.5 | 8 | 97.7 | 97 |
| 11 | H$_2$SO$_4$ (80% pure) | 0.2 | 8 | 97.9 | 98 |

Table 1-continued

Yields and silylation activities of N,N'-bis-trimethyl-silylurea prepared by the method of the invention with various catalysts, showing start-up and reaction times.

| Example No. | Catalyst | Start-up time (h) | Reaction time (h) | Yield % | Silylation activity % |
|---|---|---|---|---|---|
| 12 | H₃PO₄ | 0.5 | 8 | 98.4 | 98 |
| 13 | HBr | 0 | 5 | 98.8 | 100 |

EXAMPLE 14

A paddle drier of Loedige Model DVT-130, equipped with a jacket for steam or cooling water, a continuously variable stirrer drive, a reflux or distillate cooler, a distillate receiver and an ammonia absorber, is charged with 12 kg of urea (tech., 3 mm diam., 0.3% moisture content) and 65 kg of 96% hexamethyldisilazane containing 12 ppm of hydrogen chloride. The stirrer is driven at 45 rpm and the jacket is heated with 6 atmospheres gauge pressure of steam. As soon as the temperature of the mixture rises above 70° C it begins to react. Finally, a boiling and refluxing temperature of 114° to 115° C establishes itself, at which the reaction completes itself within 4 hours (as indicated by the increase of the internal temperature to about 125° C and the cessation of the forming of ammonia). At this moment the refluxing is shut off at the condenser and the outlet is opened, so that the excess hexamethyldisilazane distills off into the receiver. Finally the product is finish-dried briefly at 200 Torr. In all, about 32 kg of distillate is obtained having a boiling point of 126° C. The N,N'-bis-trimethylsilylurea remaining in the vessel is cooled by changing from steam to cooling water in the jacket, and is removed through the bottom drain valve. The yield amounts to 40.6 kg (99.5%) of white needles of a melting point of 231° C.

The product contains less than 0.1% of trimethylsilylisocyanate, less than 0.02% of hexamethyldisilazane, and less than 0.02% of hexamethyldisiloxane. The silylation activity amounts to 99% (plus or minus 1%).

EXAMPLE 15

A stirring boiler of a capacity of 730 liters, equipped with a jacket for steam or cooling water, a wall-riding anchor stirrer, a reflux condenser discharging into a distillate condenser, a distillate receiver and an ammonia absorber, is charged with 75 kg of urea (tech., diam. 3 mm, moisture content 0.3%) and with 320 kg of 95% hexamethyldisilazane containing 2 ppm of trimethylchlorosilane. The stirrer is driven at 11 rpm, and the jacket is heated with 6 atmospheres gauge pressure of steam. The mixture starts to react as soon as the temperature rises above 86° C. Finally, a boiling and refluxing temperature of 115° to 116° C establishes itself, at which the reaction is completed within 7 hours. Then the reflux condenser is taken out of operation so that the excess hexamethyldisilazane distils off. Finally the product is briefly finish-dried at 200 Torr. In all, 118 kg of distillate is obtained with a boiling point of about 125° C. The N,N'-bis-trimethylsilylurea remaining in the boiler is cooled by changing the jacket over from steam to cooling water, and is removed through the bottom drain valve. The yield amounts to 249.8 kg (98.2%) of white needles of a melting point of 230° to 231° C.

The product contains less than 0.1% of trimethylsilylisocyanate, less than 0.02% of hexamethyldisilazane and less than 0.02% of hexamethyldisiloxane. The silylation activity is 98.4% (plus or minus 1%).

What is claimed is:

1. In a process for preparing N,N'-bis-trimethylsilylurea by contacting urea with hexamethyldisilazane at elevated temperature sufficient to evolve ammonia, the improvement which comprises carrying out the process in the presence of an acid catalyst, which acid catalyst is a Lewis acid or a hydrogen ion yielding acid.

2. A process according to claim 1 wherein the acid catalyst is present in the reaction medium in a concentration of 20 ppb to 2 grams per liter of reaction medium.

3. A process according to claim 2 wherein the catalyst is present in an amount of 200 ppb to 200 ppm.

4. A process according to claim 1 wherein a Lewis acid is employed said Lewis acid being a compound of the halogen of an element of the third to fifth main group of the periodic system.

5. A process according to claim 1 wherein a hydrogen ion yielding acid is employed said hydrogen ion yielding acid being a hydrogen halide, sulfuric acid, phosphoric acid or an organic carboxylic acid.

6. A process according to claim 5 wherein an organic carboxylic acid is employed said organic carboxylic acid being formic acid or acetic acid.

7. A process according to claim 1 wherein the N,N'-bis-trimethylsilylurea obtained is purified with stirring by means of stirring devices for solids accompanied by the distillation off of the volatile portions of the reaction medium.

8. A process according to claim 7 wherein the stirring device employed is a wall-riding anchor stirrer.

9. A process according to claim 7 wherein the stirring device is a single-stage or multi-stage paddle stirrer.

10. A process according to claim 7 wherein the stirring device is a shovel stirrer.

* * * * *